United States Patent
Igarashi

Patent Number: 5,669,930
Date of Patent: Sep. 23, 1997

[54] STENT FOR INTRACORPOREAL RETENTION

[75] Inventor: Akira Igarashi, Yokohama, Japan

[73] Assignee: Fuji Systems Corporation, Tokyo, Japan

[21] Appl. No.: 560,673

[22] Filed: Nov. 20, 1995

[30] Foreign Application Priority Data

Dec. 8, 1994 [JP] Japan .................... 6-304591

[51] Int. Cl.$^6$ ............................................. A61M 29/00
[52] U.S. Cl. ............................................. 606/191; 606/198
[58] Field of Search ............................................. 606/191, 194, 606/198, 192, 195; 623/1, 12; 604/96, 107

[56] References Cited

U.S. PATENT DOCUMENTS

| | | | |
|---|---|---|---|
| 5,108,416 | 4/1992 | Ryan et al. | 606/194 |
| 5,156,620 | 10/1992 | Pigott . | |
| 5,158,548 | 10/1992 | Lau et al. | 606/198 |

FOREIGN PATENT DOCUMENTS

| | | |
|---|---|---|
| 6-277239 | 4/1994 | Japan . |
| 1732964 | 5/1992 | Russian Federation . |
| 80/01460 | 7/1980 | WIPO . |
| 89/07916 | 9/1989 | WIPO . |

Primary Examiner—Michael Buiz
Assistant Examiner—Kevin Truong
Attorney, Agent, or Firm—Flynn, Thiel, Boutell & Tanis, P.C.

[57] ABSTRACT

A stent for intracorporeal retention is inserted in a human body, for instance, inside an airway, esophagus, or bile duct, and used for preventing a bore of the internal organs described above from being occluded. With this stent, discharge from the airway does not easily adhere to, nor deposit on, the internal surface of the cylindrical body, so that the occlusion thereof can effectively be prevented and, at the same time, granulation does not easily occur and, for this reason, occlusion of the airway can be prevented, which insures a high degree of safety for a human body. This stent has a hollow cylindrical body 2 made from silicone rubber with both edges opened and the internal surface of this cylindrical body is processed in any of the following ways: (a) coating with a silicone resin, (b) adhesion of a fluorine-based resin tube, or (c) chemical deposition of polyparaxylylene or a derivative thereof and, at the same time, an external surface thereof is processed by (d) chemical deposition of polyparaxylylene or a derivative thereof or (e) by gradually rounding and tapering toward both edges with the tapered sections softer than other portions thereof.

9 Claims, 4 Drawing Sheets

STENT FOR INTRACORPOREAL RETENTION

FIELD OF THE INVENTION

The present invention relates to a stent inserted in a human body, for instance, inside an airway, esophagus, or bile duct, for preventing a bore of the internal organs as described above from being obturated.

BACKGROUND OF THE INVENTION

Conventionally, a stent made from silicone rubber is used against stenosis of an airway, such as a trachea or a bronchus, and the stent is retained at a position of stenosis to enlarge the section, thereby keeping open the airway which is otherwise closed and makes respiration difficult. A stent which has been known as the stent 01 described above is shown in FIG. 1 and has a cylindrical body 02 with both edges opened, and a plurality of small cylindrically-shaped projections 03 are arranged on the peripheral surface of this cylindrical body 02 to prevent movement of the stent after insertion. A method of inserting this stent 01 is generally performed by using a rigid broncho-scope, not shown herein, after a body has been subjected to general anesthesia. Namely, a rigid broncho-scope comprises, for instance, an external cylinder and an introducer, and bronchoscopy is generally performed by compressing the stent in its radial direction, inserting the compressed stent into an introducer, then inserting the introducer into the external cylinder of a rigid broncho-scope, and pushing out the stent 01 therefrom with a pusher.

Figure 1:
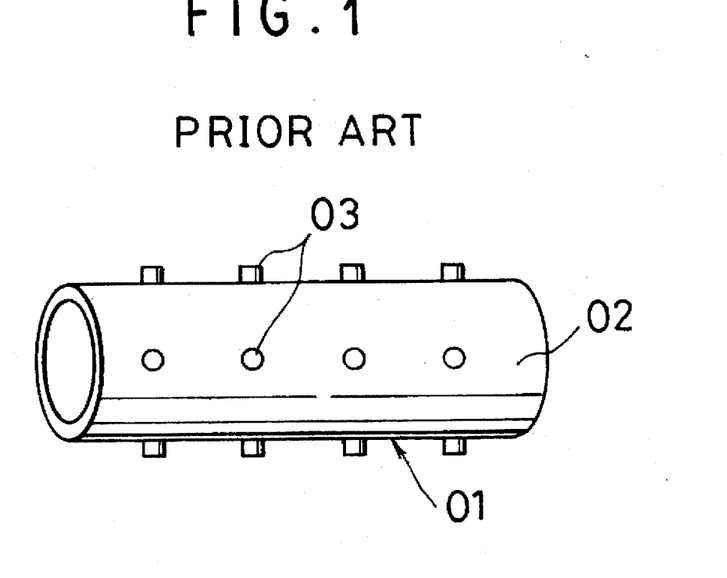
FIG. 1 is a perspective view showing a conventional type of stent.

The conventional type of stent 01 described above has such advantages that the stent can safely be retained in a bore of the internal organs, and can be taken out or exchanged with a new one after initial insertion but, on the other hand, the stent also has the danger that discharges from the airway easily adhere to and deposit on the internal surface of the cylindrical body 02, and the cylindrical body is sometimes occluded thereby. It has also the danger that sometimes granulation occurs at a position where the cylindrical body 02 and the site of stenosis contact each other because both edges of the cylindrical body 02 stimulate the tissue of the trachea or bronchus at positions contacted by the edges constantly during respiratory movement, and once granulation starts and develops, the airway may become occluded by the granulation.

OBJECTS AND SUMMARY OF THE INVENTION

The present invention was made in light of the circumstances described above and it is an object of the present invention to provide a stent which is extremely safe in a human body because a discharge from an airway hardly adheres to and deposits on the internal surface of a cylindrical body and thus the cylindrical body can be prevented from being occluded thereby, and also because granulation does not easily occur at the edges of the cylindrical body and thus the airway can be prevented from being occluded thereby.

The stent according to the present invention has a hollow cylindrical body made from a silicone rubber with both edges opened for achieving the object described above and the internal surface of this cylindrical body is processed in any of the following ways: (a) it is coated with silicone resin, (b) a fluorine-based resin tube is adhered thereto, or (c) it has a chemically deposited layer of polyparaxylylene or a derivative thereof and, at the same time, the external surface thereof is processed in either of the following ways: (d) it has a chemically deposited layer of polyparaxylylene or a derivative thereof and (e) it is gradually rounded and tapered toward its edges with the tapered sections being softer than other portions thereof. If the internal surface of the cylindrical body is formed as described above, the internal surface thereof is flexible, resistant to adhesion of discharge from the airway, and excellent in lubricity, Also, if the external surface of the cylindrical body is formed as described above, the external surface thereof provides less stimulation to the tissue in the trachea and, for this reason, granulation does not easily occur. The silicone resin coating the internal surface of the cylindrical body comprises a block polymer having a resin segment and an oil segment in the same molecule, and this block polymer solution is prepared as follows. A silane having a hydrolytic group, indicated by $RSiX_3$, is added to an organic solution of a block polymer obtained by mixing a liquid-phase dimethylpolysiloxane (A) having end reactivity and a reactive oligomer (B) including an SioH group obtained by hydrolyzing $C_6H_5SiCl_3$ in an organic solution at a mixing ratio of A/B=10/90 to 90/10 weight), preferably at a mixing ratio of A/B=60/40 to 80/20 (by weight), and thermally condensing the mixture in an organic solvent so that the ratio of the silane therein becomes X/OH>>1, and with the operation described above, the target crosslinkable block polymer solution can be obtained.

Above, R is selected from a monohydrocarbon group, and X is selected from among:

Furthermore, to increase the lubricity and prevent the adhesion of the discharge from the airway, the internal surface of the cylindrical body is coated with a solution obtained by adding a high-viscosity silicone oil having a viscosity preferably within the range of from 10,000 to one million CS, in an amount of 0.01 g to 3.5 g, and preferably 0.5 g to 1.5 g, to 100 ml of a solution of a silicone resin (percentage of nonvolatile ingredients: 23%), which is a solution of the cross-linkable block polymer described above, sufficiently dissolving it therein, and then thermally hardening the coating. Dimethyl silicone oil is suited for the silicone oil to be used herein, but it is not limited thereto. Also, a silicone oil having a higher-viscosity than one million CS can be used for this purpose without causing any problems. If this silicone oil is excessively added thereto, the strength of the coating layer becomes extremely low and, also, the adhesiveness of the coating lowers, which is not preferable because the coating easily peels off, or hardening faults occur in the coating layer. Raw rubber, which is a high polymer methylpolysiloxane of silicone, may be used in place of the silicone oil described above, but dissolving the raw rubber silicone resin solution (percentage of nonvolatile ingredients: 23%) takes a long time, which is not preferable in practical use, so that it is convenient to use silicone raw rubber dissolved in silicone oil. In this case, an increase in adhesiveness can similarly be achieved by coating with a solution obtained by adding, for instance, raw rubber dissolved in silicone oil, with a raw rubber content of 20% to 100 ml of silicone resin solution (percentage of nonvolatile ingredients: 23%), in an amount of 0.01 g to 10 g, preferably 1g to 7 g, and, for this reason, adhesion of the discharge from the airway to the internal surface thereof can be prevented.

Also, a solution such as an organic solution in which raw rubber is previously dissolved may be used in place of the raw rubber dissolved in silicone oil as described above.

It is desirable that the fluorine-based resin tube adhered to the internal surface of the cylindrical body have a thickness of 0.01 mm to 0.3 mm. The resin used for this purpose is not always limited to a fluororesin and any type of resin may be used so long as it is a fluorine-based resin. By chemically depositing paraxylylene, or a derivative thereof, on the peripheral surface of the cylindrical body, a capability of suppressing formation of granulation not obtained with silicone rubber can be obtained. Also, the external surface of the cylindrical body, which is gradually rounded and tapered towards its edges, with the tapered sections being softer than other portions, insures the tendency to suppress the occurrence of granulation, which cannot be achieved with a silicone rubber having a homogeneous hardness throughout its entire body. A soft portion can be at any location on the external surface of the cylindrical body as long as it is in contact with the tissue of the trachea, but it is especially desired to provide the soft sections at both edges, As described above, with the present invention, it is possible to obtain a stent in which the discharge from the airway does not easily adhere to the internal surface of the cylindrical body, the external surface thereof hardly stimulates the trachea tissue, and granulation is not easily formed thereon. Also, the discharge from the airway cannot easily adhere to, nor deposit on the internal surface of the cylindrical body, so that the occlusion thereof can effectively be prevented and, at the same time, granulation does not easily occur. For this reason, occlusion of the airway can be prevented, which insures a high degree of safety for the human body.

In a stent prepared according to one of the preferred modes for carrying out the present invention, a silicone resin layer is formed so that it covers an internal surface of the cylindrical body, an external surface of each edge section is notched, a silicone rubber layer softer than the cylindrical body is formed at each of the notched sections, and an external surface of the silicone rubber layer is gradually rounded and tapered toward the edge. Also, in a stent prepared according to another mode for carrying out the present invention, a fluorine-based resin layer is formed so that it covers an internal surface of the cylindrical body, an external surface of each edge section is notched, a silicone rubber layer softer than the cylindrical body is formed at the notched section, and an external surface of the silicone rubber layer is gradually rounded and tapered toward the edge. Also, in a stent prepared according to a different mode for carrying out the present invention, an external surface of each edge section of the cylindrical body is notched, a silicone rubber layer softer than the cylindrical body is formed at the notched section, an external surface of the silicone rubber layer is gradually rounded and tapered toward the edge, and a layer made from polyparaxylylene, or a derivative thereof, is formed so that it covers an internal and external surface of the cylindrical body, including the silicone rubber layer. Also, in a stent prepared according to another mode for carrying out the present invention, a fluorine-based resin layer is formed so that it covers an internal surface of the cylindrical body, an external surface of each section is notched, a silicone rubber layer softer than the cylindrical body is formed at the notched section, an external surface of the silicone rubber layer is gradually rounded and tapered toward the edge, and a layer made from polyparaxylylene, or a derivative thereof, is formed so that it covers an external surface of the cylindrical body, including the silicone rubber layer. In a stent prepared according to another mode for carrying out the present invention, peripheral ribs for positioning and preventing movement of the stent after insertion are provided at both side sections on an external surface of the cylindrical body. As a peripheral rib of this stent, it is desirable to provide a circular rib or an arculated rib having a portion notched in the peripheral direction thereof so that the cylindrical body can be compressed in the radial direction thereof. The peripheral rib may be monolithically formed with the cylindrical body. In the case of a stent of this mode, the stent is inserted into a rigid broncho-scope in its compressed state and the bronchoscope is inserted into a human body passageway, such as a trachea, and can be retained therein, which insures a further convenience. In addition, it is possible to insert the stent, when compressed, into a rigid broncho-scope having a thinner bore, so that the scope of use of the stent is widened, which is extremely useful for patients as well.

DETAILED DESCRIPTION OF THE PREFERRED EMBODIMENTS

Figure 2:
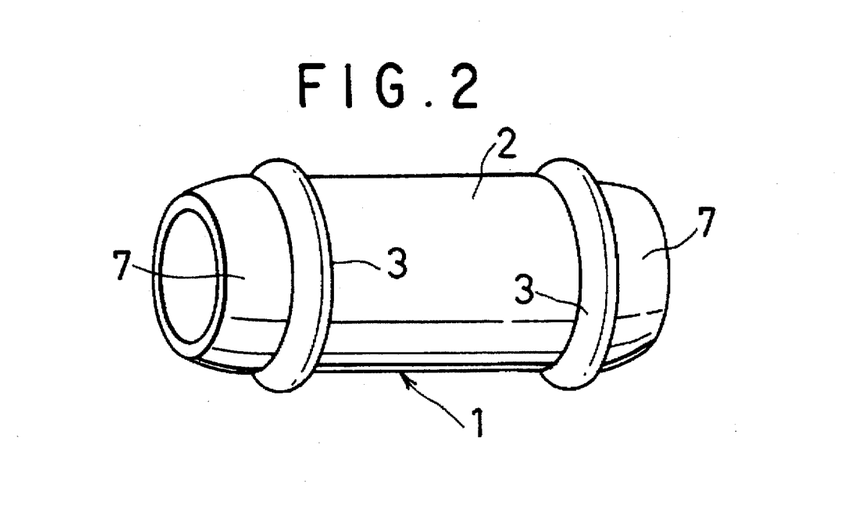
FIG. 2 is a perspective view showing a stent according to one of the most preferred embodiments of the present invention.
Figure 3:
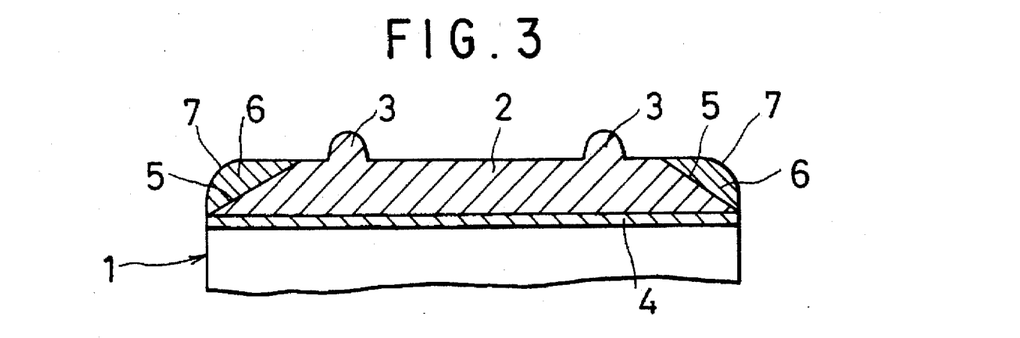
FIG. 3 is a partially enlarged vertical sectional view showing a stent.

In FIG. 2 and FIG. 3, the reference number 1 indicates a stent, which has a hollow cylindrical body 2 made from silicone rubber with both edges opened, and circular ribs 3, each as a peripheral rib, are monolithically provided at both edges of the external surface thereof. The rib 3 has the function of preventing movement of the stent 1 after insertion similar to the projection 03 in conventional stouts. A silicone resin layer 4 is formed by coating a silicone resin on an internal surface of the cylindrical body 2 so that it covers the internal surface thereof. Also, the external surface of each edge of the cylindrical body 2, which is located outward from the rib 3, is notched with an inward inclination and a silicone rubber layer 6 softer than the cylindrical body 2 is adhered to the notched section 5 with an adhesive. The external surface 7 of the silicone rubber layer 6 is gradually rounded and tapered toward the edge.

Description will now be made of an example of preparation of the stent 1. Fifteen parts of barium sulfate and 1.3 parts of a vulcanizing agent are added to 100 parts of silicone rubber KE1551U having a hardness of 55 (JIS K6031 A type), produced by SHIN'ETSU CHEMICAL INDUSTRY CO., and an unvulcanized silicone rubber sheet well-mixed by a roll is molded in a mold for a stent and pressed by a press at a temperature of 130° C. for 15 minutes, and then the mold is opened to pull out a core metal from the stent 1 made from silicone rubber, which is a molded product, and a stent 1 made from silicone rubber having its external surface 7 of each edge gradually rounded and tapered toward the edge as shown in FIG. 2 can be obtained. This stent 1 is subjected to an after vulcanization in an oven at a temperature of 180° C. for eight hours to remove reactive residues therefrom. Then, the external surface of each edge of this stent 1 is trimmed and notched with an inward inclination toward the bore of the stent by a grinding machine such as a grinder, and a silicone rubber layer 6 with a hardness of 1 (JIS K6301 A type) is adhered to this notched section 5. After this step, the internal surface of the stent 1 is coated with a solution of a silicone resin in the order of 1), 2) and 3) as described below.

1) A silicone resin solution with a content of nonvolatile ingredients of 23% comprising a block polymer having a resin segment and an oil segment in one molecule.

2) A solution obtained by adding 1.5 g of silicone oil KF96H—100,000 with a viscosity of 100,000 CS to 100 ml of the silicone resin solution 1) described above and sufficiently agitating and dissolving therein.

3) A solution obtained by adding 5 g of a raw rubber dissolved in a silicone oil with a raw rubber content of 20% to 100 ml of the silicone resin solution of 1) described above and sufficiently agitating and dissolving it therein.

After coating with these solutions, the coating is sufficiently air-dried and the solvent therein volatized, and then heated for hardening in an oven at a temperature of 160° C. for one hour, wherein a silicone resin layer 4 is formed in which the discharge from the airway does not easily adhere to the internal surface thereof.

Because a silicone rubber layer 6 with a hardness of 1 (JIS K6301 A type) is formed on the external surface of each edge of the stent 1 as described above, the external surface thereof becomes softer than the cylindrical body 2, which insures an excellent capability to suppress the formation of granulation. Namely, a silicone rubber layer 6 softer than the cylindrical body 2 is provided on the external surface of each edge thereof and the force generated when each edge of the cylindrical body 2 mechanically contacts the internal surface of a trachea is made weaker thereby, and for this reason, it becomes possible to delay and suppress the formation of granulation. In the case where the external surface of each edge of the cylindrical body 2 is notched for tapering, the force generated from contacting the internal surface of a trachea can be made weaker, but if there are sharp edges on the surface, the edges stimulate the internal surface of the airway, which is not preferable. Also, if the edge section is thin, it is weakened in strength and easily deformed toward the side of the bore of the cylindrical body, which is also undesirable. Namely, it is desirable that the edge section is appropriately round and soft enough to enable the weakening of the force generated from contact with the internal surface of the trachea and has an appropriate strength for the edge section not to be easily deformed toward the bore of the stent. Generally, to provide the hardness (JIS K6301 A type) required for a trachea stent, a silicone rubber with a hardness of approximately 60 is used, so the softer silicone rubber provided on the external surface of each edge should have a hardness of less than 30 of the JIS K6301 A type, and preferably of less than 10, and in the case where a silicone gel softer than a silicone rubber is used, it is desirable that the degree of insertion with a pin (hardness) is less than 150, and preferably less than 100 under the conditions of JIS K2220, ¼ cone, and the whole load of 9.38 g. But, if the hardness thereof becomes too low, the mechanical strength sometimes lowers, with the adhesive force weakened, and a tack touch appears on the surface thereof, which is not preferable.

Figure 4:
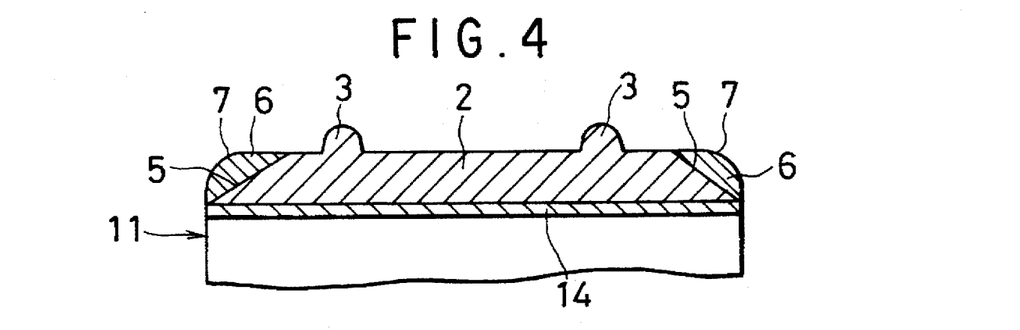
FIG. 4 is a partially enlarged vertical sectional view showing a stent according to Embodiment 2 of the present invention.

FIG. 4 is a partially enlarged vertical sectional view showing a stent according to Embodiment 2 of the present invention. This stent 11 is different from that according to Embodiment 1 in that a fluorine-based resin layer 14 is formed on the internal surface 2 of the cylindrical body 2 in place of the silicone rubber layer 4 described above, but the remainder is the same as in Embodiment 1. The fluorine-based resin layer 14 is formed by, for instance, adhering a tube made from a fluorine-based resin to the internal surface of the cylindrical body 2.

Description will now be made of an example of preparation of a stent 11. 4.0 parts of a vulcanizing agent C-4 is added to 100 parts of a silicone rubber KE54OU having a hardness of 40 produced by SHIN'ETSU CHEMICAL INDUSTRY CO. and an unvulcanized rubber sheet mixed sufficiently by a roll is prepared. Then, a silane-based primer for a silicone rubber is applied to the external surface of a tube made from fluororesin PFA (a copolymer of tetrafluoroethylene -perfluoroalkylvinylether) having an outer diameter of 8.0 mmΦ, a wall thickness of 0.05 mm, and a length of 30 mm, said external surface having been subjected to processing with an ammonia solution of metallic sodium, and air-dried. Then, a core metal with an outer diameter of approximately 7.90 mmφ is inserted into a bore of this tube made from PFA without a clearance between them. The unvulcanized silicone rubber sheet described above is placed in the space of the stent mold by using the core metal covered by the PFA tube, pressed by a press under a temperature of 170° C. for 20 minutes to thermally harden the silicone rubber and, at the same time, the silicone rubber is hardened and adhered to the external surface of the PFA tube. Then, after pressing, the mold is opened, and the core metal is pulled out from the tube-shaped stent 11 made from silicone rubber with the PFA tube adhered to the internal surface thereof, and the stent 11 made from silicone rubber comprising a thin tube made from PFA with the internal surface covered with fluororesin is obtained. This stent is subjected to an after vulcanization in an oven at a temperature of 180° C. for eight hours to remove reactive residues. Then, the external surface of each edge of this stent 11 is notched as in Embodiment 1, and the silicone rubber layer 6 is adhered thereto.

The thickness of the tube made from fluororesin at its internal surface is in a range from 0.01 mm to 0.3 mm as described above, and preferably in a range from 0.03 mm to 0.1 mm. If it is less than the value described above, it is difficult to produce a tube and the physical strength thereof becomes weak, and if the thickness is more than the value described above, the flexibility of the stent 11 is reduced and the stent does not conform to biological tissue such as the trachea. The tube made from silicone rubber is inserted so that it contacts the internal surface of this stent 11 to mask the internal surface of the stent, and then a thin film of poly-monochloro-para-xylylene is provided on the external surface thereof. After the thin film has been provided thereon, the tube described above is removed.

Figure 5:
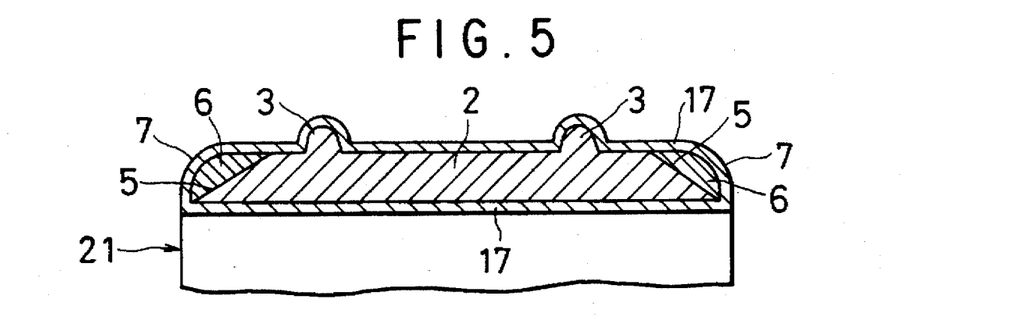
FIG. 5 is a partially enlarged vertical sectional view showing a stent according to Embodiment 3 of the present invention.

FIG. 5 is a partially enlarged vertical sectional view showing a stent according to Embodiment 3 of the present invention. This stent 21 is different from Embodiment 2 in that a layer 17 of poly-monochloro-paraxylylene, which is one of the derivatives of polyparaxylylene, is formed in the internal and external surface of the cylindrical body 2 in place of the fluorine-based resin layer 14 described above so that it covers the internal and external surface thereof, and portions other than that are the same as those in Embodiment 2. The layer 17 of poly-monochloro-para-xylylene is formed by chemically depositing poly-monochloro-para-xylylene in the internal and external surface of the cylindrical body 2.

Description is made for an example of preparation of a stent 21. Poly-monochloro-para-xylylene, which is a derivative of polyparaxylylene, is chemically deposited on the internal and external surfaces of the cylindrical body 2 by using a molded stent as in Embodiment 1 in the following processing sequence: ① vaporization of a dimer from poly-monochloro-para-xylylene having been subjected to chemical deposition in a vaporization room→② generation of diradical-monochloro-para-xylylene by thermally decomposing the dimer in a thermal decomposition room→③ adsorption of diradical-monochloro-para-xylylene and formation of a strong deposition of a thin film made from polymerized and high molecular weight poly-monochloro-para-xylylene to the internal and external surfaces of the cylindrical body 2→④ an exhausting process. A stent 21 made from silicone rubber is obtained according to the sequence described above. As the thickness of a thin film deposited by polyparaxylylene or a derivative thereof, a range from 0.01 μm to 20 μm m is required and, preferably, a range from 0.1 μm to 5 μm is more preferable. If the film is too thin, its lubricity becomes too low and, on the other hand, if it is too thick, the deposited film has less flexibility and, for this reason, when it is bent, cracking occurs therein, which is disadvantageous in practical use. Discharge from an airway is prevented from adhering to and depositing on the internal surface of a stent 21 and granulation occurring between the external surface of each edge of the stent 21 and the internal surface of the trachea can be delayed or suppressed by the lubricity of the surface, which also has an excellent chemical resistance not obtained with silicone rubber and an adaptability to a living body which prevents the deposition of this polyparaxylylene, or a derivative thereof, to the internal and external surface of the stent 21 made from silicone rubber.

Figure 6:
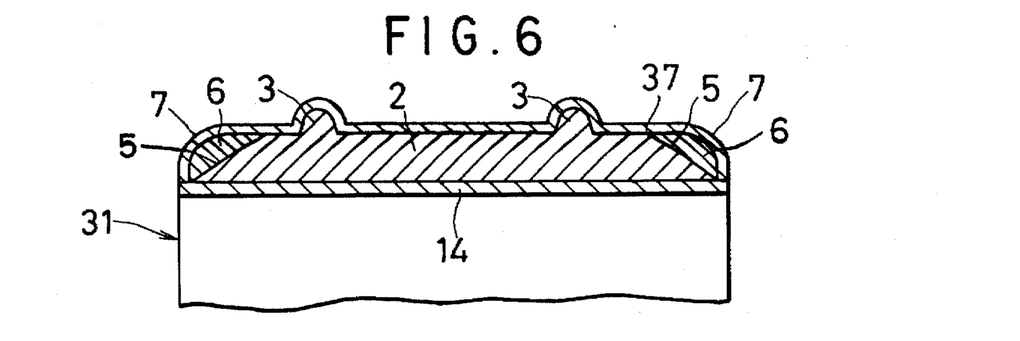
FIG. 6 is a partially enlarged vertical sectional view showing a stent according to Embodiment 4 of the present invention.

FIG. 6 is a partially enlarged vertical sectional view showing a stent according to Embodiment 4 of the present invention. This stent 31 is different from Embodiment 2 in that polyparaxylylene, or a derivative thereof, layer 37 is formed on the external surface of the cylindrical body 2 according to Embodiment 2, and positions other than that are the same as those in Embodiment 2.

Figure 7A:
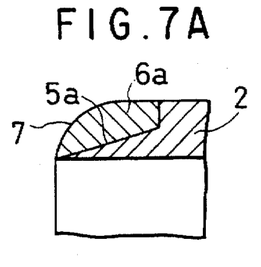
FIG. 7A to FIG. 7E are partial sectional views Showing modifications to a notched section and a silicone rubber layer of the cylindrical body.
Figure 7B:
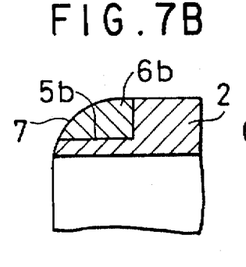
Figure 7C:
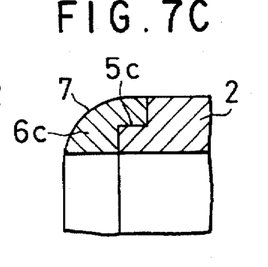
Figure 7D:
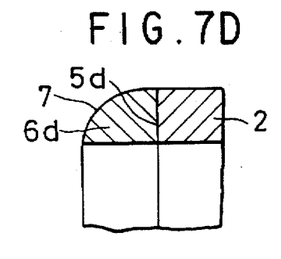
Figure 7E:
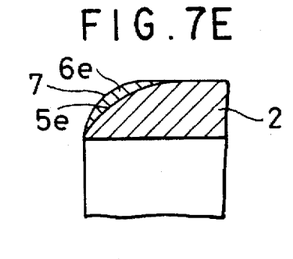

A shape of the notched section 5 and a shape of silicone rubber layer 6 formed therein in each embodiment described above indicate only an example and, needless to say, any shape other than those shown in the figures may be employed. FIG. 7A to FIG. 7E are each modifications thereof, and in FIG. 7A, the notched section 5a is formed by two faces; one face perpendicular to the axis extending from the external surface to the side of the internal surface thereof and another face extending from the edge of the internal surface to a downward inclination, and a silicone rubber layer 6a conforming thereto is adhered and formed in the section. In FIG. 7B, the notched section 5b is formed by two faces; a face perpendicular to the axis extending from the external surface to the side of the internal surface and another face extending in parallel to the axis from the edge of the internal surface, and a silicone rubber layer 6b conforming thereto is adhered and formed in the section. In FIG. 7C, the notched section 5c is formed by three faces; a face perpendicular to the axis extending from the external surface to the side of the internal surface, a face extending in parallel to the axis from the edge of the internal surface, and a face perpendicular to the axis extending from the edge of the end to the side of the internal surface, and a silicone rubber layer 6c conforming thereto is adhered and formed in the section. In FIG. 7D, the notched section 5d is formed by faces perpendicular to the axis extending from the external surface to the side of the internal surface, and a silicone rubber layer 6d conforming thereto is adhered and formed in the section. In FIG. 7E, the notched section 5e is formed by a curved face extending from the external surface to the internal surface, and a silicone rubber layer 6e conforming thereto is adhered and formed in the section.

Figure 8:
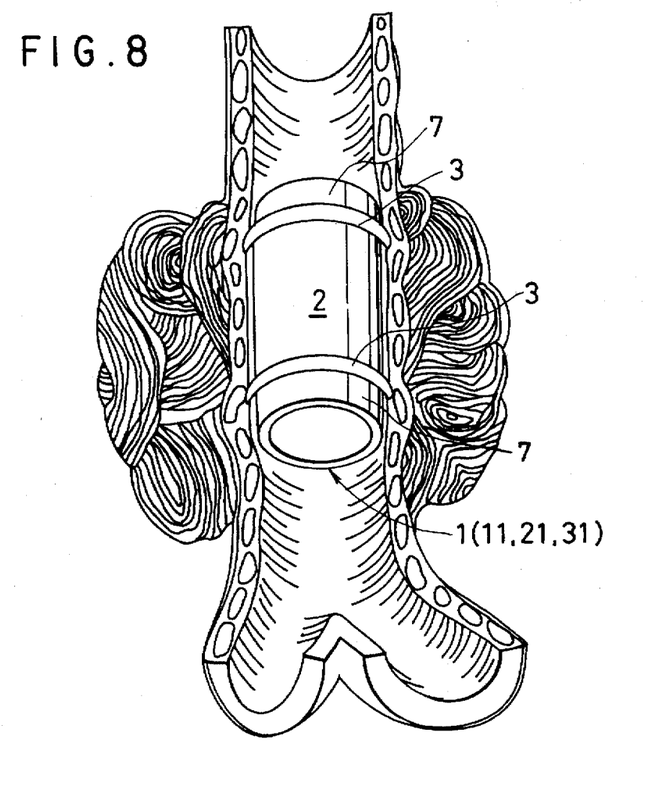
FIG. 8 is an explanatory view showing the effects thereof.

FIG. 8 shows stents 1, 11, 21 and 31 according to each embodiment described above in a retained state in a section of a trachea with stenosis by pushing out each of the stents by a rigid broncho-scope under general anesthesia and by inserting it thereto. As clearly understood from FIG. 8, each rib 3 has a function so that it is engaged in the internal surface of a bore of a tracheal section with stenosis and prevents movement of each of the stents 1, 11, 21 and 31, and with this function to prevent movement, the stent enlarges the tracheal section with stenosis and prevents it from being occluded.

It should be noted that each embodiment shown in the figures is provided only as a preferable example, and each embodiment described above is not intended to limit this invention. Namely, it is also possible to obtain the same effect as that obtained in each embodiment, for instance, by covering the internal surface of the cylindrical body 2 with a silicone resin layer 4 and by covering the external surface with a polyparaxylylene layer 37, and, also, a configuration is permitted wherein an external surface of each edge of the cylindrical body 2 is notched, and a soft silicone rubber layer 6 is formed in the notched section in each embodiment and, furthermore, a layer 17 made from poly-monochloro-para-xylylene may be employed in place of the configuration described above.

Figure 9:
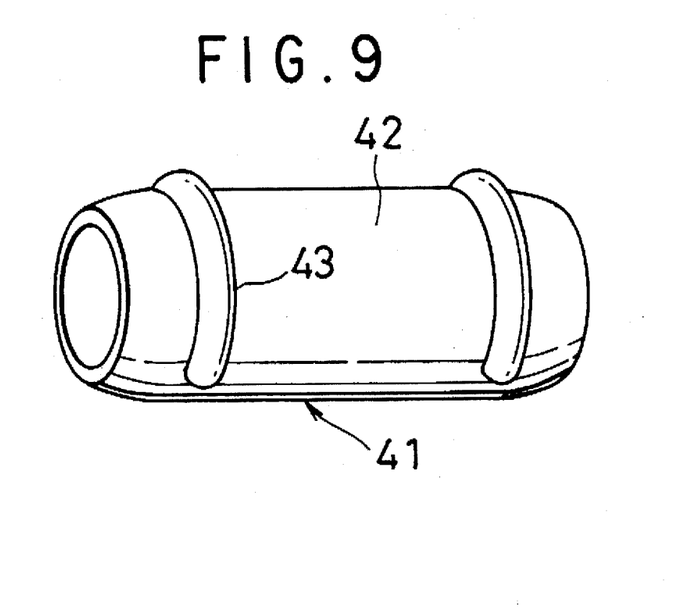
FIG. 9 is a perspective view showing a stent according to Embodiment 5 of the present invention.
Figure 10:
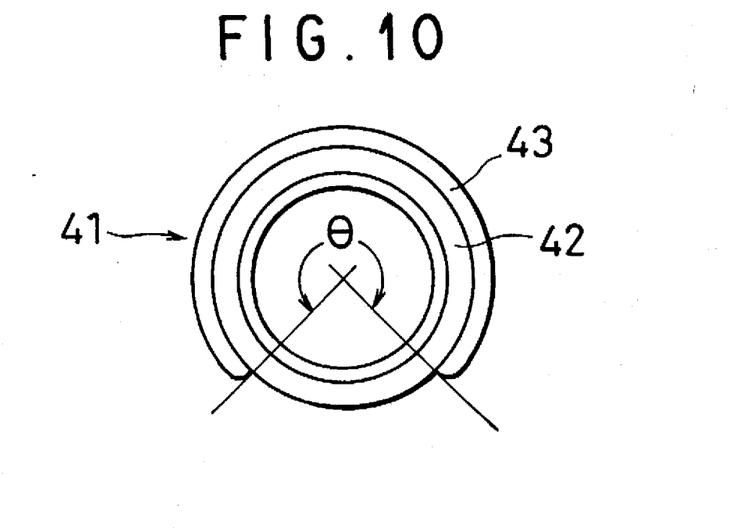
FIG. 10 is an enlarged side view of FIG. 9.

FIG. 9 is a perspective view showing a stent as a whole according to Embodiment 5 using a rib different from that in the embodiments described above, and FIG. 10 is an enlarged side view thereof. An arculated rib 43 as a peripheral rib of the stent according to this embodiment also has a positioning function to prevent movement of the stent after being inserted, which is the same as that in each embodiment. The rib 43 is provided in an arculated shape with a portion in the peripheral direction thereof being notched so that the cylindrical body can be compressed in the radial direction thereof on each side of the edges of the external surface of the cylindrical body 42, It is assumed that an angle in the peripheral direction where the rib 43 is provided is set in a range from 180° to 300°, which is desirable for compressing the cylindrical body 42. Also, this rib 43 is provided monolithically with the cylindrical body and it is not necessary to limit the shape to the form described above, and, for instance, the rib may be adhered to the cylindrical body with an adhesive after each of them has been formed discretely. Figure for configuration of a cylindrical body 42 other than the rib 43 is omitted herein, but any configuration in each embodiment described above may be employed.

In the case of the stent 41 having the rib 43 described above, when the stent is to be inserted into a section of trachea with stenosis, it is possible to insert it into an introducer for a rigid broncho-scope in a state where the stent has been compressed in the radical direction thereof and, for this reason, the insertion thereof becomes easier than that with stents 1, 11, 21 and 31 in each embodiment described above.

What is claimed is:

1. A stent for intracorporeal retention inside a bore of an internal organ to prevent the occlusion thereof, said stent comprising a hollow, elongated cylindrical body having internal and external surfaces and open edge portions provided at opposing ends thereof, the hollow, elongated cylindrical body being made of a silicone rubber, the internal surface of said hollow, elongated cylindrical body having a member selected from the group consisting of a silicone resin coating provided thereon, a fluorine-based resin tube adhered thereto, a layer of polyparaxylylene, and a layer of poly-monochloro-para-xylylene, deposited thereon and the external surface of said hollow, elongated cylindrical body having either polyparaxylylene, or poly-monochloro-para-xylylene deposited thereon or portions of said external surface adjacent said edge portions gradually rounded and tapered toward said edge portions and softer than other portions of said external surface.

2. A stent according to claim 1, wherein said silicone resin is coated on the internal surface of the cylindrical body, an external surface of each edge portion is notched, a silicone rubber layer softer than the cylindrical body is formed in each of the notched portions, and an external surface of said silicone rubber layer is gradually rounded and tapered toward the edge portions.

3. A stent according to claim a, wherein said fluorine-based resin is adhered to the internal surface of the cylindrical body, an external surface of each edge portion is notched, a silicone rubber layer softer than the cylindrical body is formed in the notched portions, and an external surface of said silicone rubber layer is gradually rounded and tapered toward the edge portions.

4. A stent according to claim 1, wherein an external surface of each edge portion of the cylindrical body is notched, a silicone rubber layer softer than the cylindrical body is formed in said notched portions, an external surface of said silicone rubber layer is gradually rounded and tapered toward the edge portions, and a layer made from polyparaxylylene, or a poly-monochloro-para-xylylene, covers an internal and external surface of the cylindrical body, including said silicone rubber layer.

5. A stent according to claim 1, wherein said fluorine-based resin is adhered to the internal surface of the cylindrical body, an external surface of each edge portion is notched, a silicone rubber layer softer than the cylindrical body is formed thereon, an external surface of said silicone rubber layer is gradually rounded and tapered toward the edge portions, and a layer made from polyparaxylylene, or a poly-monochloro-para-xylylene, covers an external surface of the cylindrical body including said silicone rubber layer.

6. A stent according to claim 1, wherein peripheral ribs for positioning and preventing movement of said stent after retention are provided on said edge portions.

7. A stent according to claim 6, wherein said peripheral ribs are circular ribs.

8. A stent according to claim 6, wherein said peripheral ribs are arculated ribs with a portion in the peripheral direction thereof notched so that the cylindrical body can be compressed in the radial direction thereof.

9. A stent according to claim 6 wherein said peripheral ribs are monolithically formed with the cylindrical body.

* * * * *

UNITED STATES PATENT AND TRADEMARK OFFICE
CERTIFICATE OF CORRECTION

PATENT NO. : 5 669 930
DATED : September 23, 1997
INVENTOR(S) : Akira IGARASHI

It is certified that error appears in the above-indentified patent and that said Letters Patent is hereby corrected as shown below:

Column 9, line 30; change "claim a" to ---claim 1---.

Signed and Sealed this

Twenty-fourth Day of March, 1998

*Attest:*

BRUCE LEHMAN

*Attesting Officer*   *Commissioner of Patents and Trademarks*